US00PP27104P2

(12) United States Plant Patent
Kordes

(10) Patent No.: US PP27,104 P2
(45) Date of Patent: Aug. 30, 2016

(54) FLORIBUNDA ROSE PLANT NAMED 'KORBYLOSANG'

(50) Latin Name: *Rosa hybrida*
Varietal Denomination: KORbylosang

(71) Applicant: Tim-Hermann Kordes, Klein Offenseth-Sparrieshoop (DE)

(72) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 91 days.

(21) Appl. No.: 14/120,938

(22) Filed: Jul. 11, 2014

(51) Int. Cl.
*A01H 5/02* (2006.01)

(52) U.S. Cl.
USPC ..... Plt./147

(58) Field of Classification Search
USPC ..... Plt./147
See application file for complete search history.

(56) References Cited

PUBLICATIONS

Rose Trials, www.worldrose.org/trials/2012/kortijk/kortijk11.asp, Jun. 29, 2012.*
Baden-Baden TV, Die "Schoene vom See" von Kordes gewinnt Ehrenpreis als Goldene Rose 2012 von Baden-Baden, http://www.baden-baden.tv/Baden-Baden/Video/2012/06/20/Die-Schoene-vom-See-von-Kordes-gewinnt-Ehrenpreis-als-Goldene-Rose-2012-von-Baden-Baden1340178334.htm, Jun. 20, 2012.*

* cited by examiner

*Primary Examiner* — Anne Grunberg

(57) ABSTRACT

A new and distinct variety of rose with long lasting, novel apricot-colored flowers, and attractive foliage with very good disease resistance. It exhibits upright to bushy growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORbylosang'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 2001. The crossing was between an un-named seedling, the seed parent, and another un-named seedling, the pollen parent by the same inventor.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORbylosang'.

SUMMARY OF THE INVENTION

The new rose plant may be distinguished from its seed parent, an un-named seedling, by the following combination of characteristics:

1. 'KORbylosang' has apricot-colored flowers, whereas the un-named seedling has yellow flowers.
2. 'KORbylosang' has a large-size flower, whereas the un-named seedling has a medium size flower.

The new rose plant may be distinguished from its pollen parent, an un-named seedling, by the following combination of characteristics:

1. 'KORbylosang' has a double petal count, whereas the un-named seedling has a very double petal count.
2. 'KORbylosang' re-blooms very quickly, whereas the un-named seedling is slow to re-bloom.

The objective of the hybridization was to create a new and distinct rose plant with unique qualities, such as:

1. Uniform growth and flowering;
2. Abundant attractive, recurrent flowers;
3. Attractive and abundant foliage; and
4. Resistance to diseases encountered in landscapes and gardens.

This combination of qualities is not present in prior rose cultivars known to the inventor. These objectives have been substantially achieved and in that distinguish 'KORbylosang' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORbylosang' was selected in May 2002 from the seedling beds to be asexually propagated for further evaluation. The first asexual propagation of 'KORbylosang' was done by budding in July 2002 at the inventor's nursery in Offenseth-Sparrieshoop, Germany.

These initial and other subsequent propagations conducted in controlled environments demonstrate that 'KORbylosang' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORbylosang'.

DETAILED BOTANICAL DESCRIPTION

The following is a description of 'KORbylosang', as observed growing in May 2014 in a nursery in Jackson County, Oreg. on plants of 3 years of age. Color references are made using The Royal Horticultural Society (London, England) Colour Chart, 2001 except where common terms of color are used.

For a comparison, several physical characteristics of the rose variety 'KORjuknei', a rose variety from the same inventor described and illustrated in U.S. Plant Pat. No. 22,499 issued on Feb. 21, 2010 are compared to 'KORbylosang' in Chart 1.

CHART 1

| Characteristic | 'KORbylosang' | 'KORjuknei' |
|---|---|---|
| Growth Habit. | Upright to bushy. | Arching. |
| General Tonality of Open Flower. | Orange-Red Group 32C. | Red Group 38C. |
| Petal Count. | 35 to 40. | 100 to 120. |

Parents:

*Seed parent*.—An un-named seedling.

*Pollen parent*.—An un-named seedling.

Classification:

*Botanical classification*.—*Rosa hybrida* 'KORbylosang'.

*Commercial classification*.—Floribunda rose.

FLOWER AND FLOWER BUD

Blooming habit: Recurrent. Prolific.

Flower bud:

*Size*.—Upon opening, 30 mm in length from base of receptacle to distal end of bud and 25 mm diameter at its widest point.

*Bud form*.—Long. Pointed ovoid.

*Bud color*.—As sepals first unfold, bud color is Yellow-Orange Group 20C with intonations of Red 46D. When ¼ open, the upper surface of petals is Orange Group 25D, and the lower surface is Yellow-Orange Group 19D.

*Sepals*.—Color: Upper surface: Yellow-Green Group 146D. Lower surface: Yellow-Green Group 146B. Size: Average 20 mm (l)×8 mm (w). Shape: Weak foliaceous appendages on 3 of the five sepals. Apex: Apiculate. Base: Flat at union with receptacle. Quantity: Five. Surface texture: Upper side: Moderately pubescent. Lower surface: Lightly pubescent with some stipitate glands. Margins: Lightly pubescent with stipitate glands. Stipitate glands: Limited.

Flower bloom:

*Fragrance*.—None.

*Duration*.—On the plant 3 to 5 days. Senesced petals drop away cleanly.

*Size*.—Medium for a floribunda rose. When open, the average flower diameter is 70 mm and the average flower height is 20 mm.

*Form*.—Shape of flower when viewed from the side: Upon opening, upper part: Flattened convex. Upon opening, lower part: Flattened convex. Open flower, upper part: Flat. Open flower, lower part: Convex.

Color:

*Upon opening, petals*.—Outermost petals: Outer Side: Yellow-Green Group 20B. Inner Side: Orange Group 24C and Orange Group 25C. Innermost petals: Outer Side: Orange Group 24C. Inner Side: Orange-Red Group 32C.

*Upon opening, basal petal spots*.—Basal petal spot, outermost petals: Outer Side: Yellow Group 3B. Inner Side: Yellow Group 9B. Basal petal spot, innermost petals: Outer Side: Yellow Group 3A. Inner Side: Yellow Group 3A.

*After opening, petals*.—Outermost petals: Outer Side: Yellow-Orange Group 18B. Inner Side: Orange Group 28D. Innermost petals: Outer Side: Yellow Orange Group 22C. Inner Side: Orange Group 28C.

*After opening, basal petal spots*.—Basal petal spot, outermost petals: Outer Side: Yellow Group 3B. Inner Side: Yellow Group 3A. Basal petal spot, innermost petals: Outer Side: Yellow Group 2B. Inner Side: Yellow Group 2A.

General tonality: On open flower Orange-Red Group 32C. No change in the general tonality at the end of the 3rd day. Afterwards, general tonality is Red Group 37D.

Petals:

*Petal count*.—Double.

*Average range*.—Approximately 35 to 40 petals under normal conditions.

*Petal reflex*.—Petals reflex slightly.

*Petal margin*.—Entire.

*Petal shape*.—Obovate. Apex: Obtuse. Base: Cuneate.

*Petal size*.—15 to 40 mm (l)×20 to 30 mm (w).

*Petal arrangement*.—Not formal. Rosette.

*Texture*.—Smooth.

Petaloids:

*Petaloid count*.—Average of 3 to 8 per flower.

*Petaloid size*.—10 to 20 mm (l)×3 to 10 mm (w).

*Petaloid color*.—Inner side: Orange Group 25C. Outer side: Yellow-Orange Group 20C.

*Petaloid texture*.—Smooth.

*Margins*.—Undulated. Indented. Irregular.

*Petaloid shape*.—Variable, from lanceolate to obovate. Apex: Acute to obtuse. Base: Attenuate.

Reproductive organs:

*Pistils*.—Average. Approximately 40 present. Stigmas: Location: Inferior in position to anthers. Color: Yellow Group 10B. Styles: Length: About 2 mm long. Color: Red Group 47C.

*Stamens*.—Approximately 70 on average and regularly arranged. Anthers: Size: Average 2 mm (l)×1 mm (w). Pollen: Generally present. Color: Greyed-Orange Group 164C. Filaments: Color: Yellow Group 9B. Length: 10 mm.

Receptacle:
*Surface*.—Smooth.
*Color*.—Yellow-Green Group 146B. Intonations of Greyed-Red Group 181C.
*Shape*.—Urn-shaped.
*Texture*.—Glabrous.
*Size*.—10 mm (h)×9 mm (w).

Pedicel:
*Surface*.—Moderate numbers of stipitate glands.
*Length*.—50 to 70 mm average length.
*Diameter*.—2 to 3 mm average diameter.
*Color*.—Yellow-Green Group 146C.
*Strength*.—Moderately strong.
*Texture*.—Rugose.
*Borne*.—Most commonly, 1 to 3 flower buds per stem. Flowers upright to slightly pendant.

Peduncle:
*Surface*.—Glabrous.
*Length*.—40 to 50 mm average length.
*Diameter*.—3 to 4 mm average diameter.
*Color*.—Yellow-Green Group 146C. Intonations of Greyed-Red Group 178B.
*Strength*.—Strong.

THE PLANT

Growth: Moderately vigorous.

Plant habit: Upright to bushy. When grown as a field plant, the average plant height is 90 cm and the average plant width is 60 cm.

Stems:
*Stem color*.—Young wood: Yellow-Green Group 146C. Older wood: Yellow-Green Group 146.
*Intonations*.—Greyed-Red Group 178C.
*Stem surface texture*.—Young wood: Smooth. Older wood: Smooth.

Prickles: Present.
*Incidence*.—Average of 10 per each 10 cm of stem.
*Size*.—Average length: 8 mm.
*Color*.—Immature prickles: Greyed-Purple Group 187C. Mature prickles: Gryed-Purple Group 183D. Senescing to Greyed-Brown Group 199B.
*Shape*.—Deeply concave.

Leaves: Normally 5 leaflets on normal leaves in middle of the stem.
*Venation pattern*.—Pyramidal net pattern.
*Leaf size*.—140 mm (l)×90 mm (w).
*Abundance*.—Average.

Leaflets:
*Size*.—Average size of the terminal leaflet is 50 mm (l)×45 mm (w).
*Shape*.—Ovate. Base: Obtuse. Apex: Cuspidate.
*Margins*.—Finely serrated.
*Surface*.—Upper: Glossy. Lower: Matte.
*Texture*.—Upper side of leaflet: Leathery. Under side of leaflet: Leathery.
*Color, mature foliage*.—Upper Leaflet Surface: Green Group 138B. Lower Leaflet Surface: Yellow-Green Group 146B.
*Color, juvenile foliage*.—Upper Leaflet Surface: Yellow-Green Group 146B. Lower Leaflet Surface: Yellow-Green Group 146C. Anthocyanin intonation: Greyed-Purple roup183A. Location: Entire leaf surface of juvenile foliage. Along the margin of more mature foliage.
*Arrangement*.—Odd pinnate.
*Venation*.—Reticulate.

Stipules:
*Size*.—25 mm (l)×4 mm (w).
*Stipule color*.—Yellow-Green Group 144A.
*Anthocyanin*.—Greyed-Red Group 181B. Located on upper side of mid-rib.
*Stipitate glands*.—Limited, along margins.
*Margins*.—With stipitate glands.
*Texture*.—Glabrous.
*Shape*.—Apex: Apiculate. Base: Winged.

Petiole:
*Length*.—Average 25 mm.
*Diameter*.—Average 2 mm.
*Petiole color*.—Yellow-Green Group 146B. Underneath: Yellow-Green Group 146B.
*Margins*.—Slightly pubescent. With stipitate glands.
*Anthocyanin*.—Greyed-Orange Group 176A.
*Prickles*.—Present.
*Stipitate glands*.—Limited.
*Texture*.—Glabrous.

Petiole rachis:
*Length*.—Average 20 mm.
*Diameter*.—Average 1.5 mm.
*Color*.—Yellow-Green Group 146C. Anthocyanin: Greyed-Orange Group 176A. Present on upper side.
*Prickles*.—A few small prickles underneath.
*Stipitate glands*.—Limited numbers of stipitate glands on margins.

Hips/seed formation: None observed.

Winter hardiness: To date, the variety has been grown successfully in Zone 6.

Disease resistance: Very good resistance to Powdery mildew (*Sphaerotheca pannosa*), blackspot (*Diplocarpon rosae*), and rust (*Phragmidium* sp) diseases under normal growing conditions in Jackson County, Oreg.

I claim:

1. A new and distinct variety of rose plant, as described and illustrated herein.

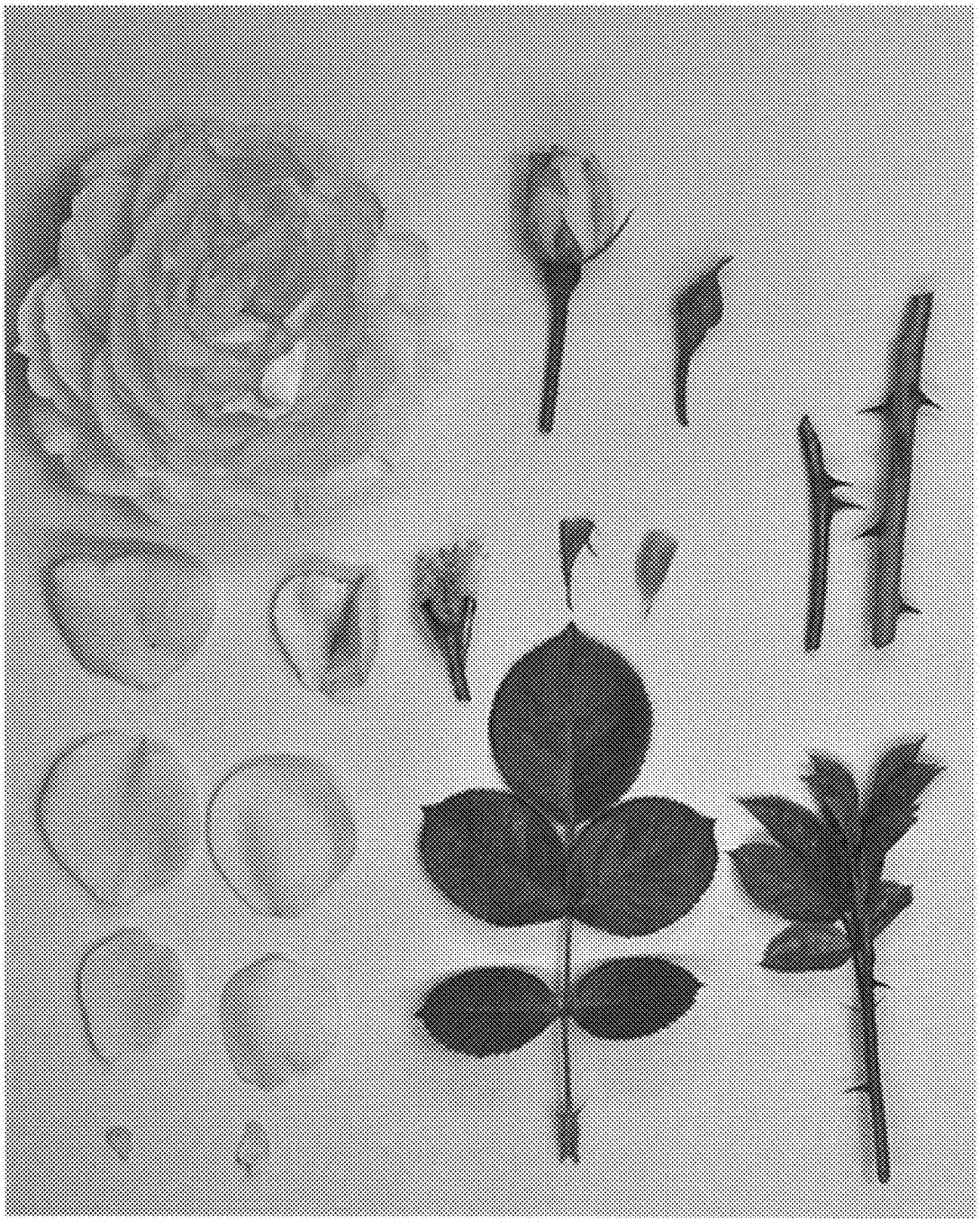

* * * * *